United States Patent [19]

Aquila et al.

[11] Patent Number: 4,720,327
[45] Date of Patent: Jan. 19, 1988

[54] DISTILLATIVE SEPARATION OF LIQUID MIXTURES OF SUBSTANCES

[75] Inventors: Werner Aquila, Mannheim; Axel Nissen, Leimen; Gerd Kaibel, Lampertheim; Michael Horner, Neustadt; Walter Rebafka, Hirschberg, all of Fed. Rep. of Germany

[73] Assignee: BASF Aktiengesellschaft, Ludwigshafen, Fed. Rep. of Germany

[21] Appl. No.: 420,485

[22] Filed: Sep. 20, 1982

[30] Foreign Application Priority Data

Sep. 26, 1981 [DE] Fed. Rep. of Germany ....... 3138423

[51] Int. Cl.4 .............................................. B01D 3/38
[52] U.S. Cl. .............................. 203/96; 203/DIG. 23; 203/DIG. 25; 568/875; 568/913
[58] Field of Search ................. 203/92, 95, 96, 91, 203/DIG. 25, DIG. 23, 3; 568/913, 875

[56] References Cited

U.S. PATENT DOCUMENTS

| | | | |
|---|---|---|---|
| 2,470,222 | 5/1949 | Patterson | 203/97 |
| 2,555,939 | 6/1951 | Sherwin | 203/97 |
| 2,961,452 | 11/1960 | Raphael | 568/875 |
| 3,303,108 | 2/1967 | Krauch et al. | 203/96 |
| 3,347,681 | 10/1967 | Platt | 426/655 |
| 3,425,935 | 2/1969 | Cahn | 203/96 |
| 3,787,593 | 1/1974 | Atkins et al. | 426/429 |
| 3,917,865 | 11/1975 | Shaw et al. | 426/492 |
| 4,029,709 | 6/1977 | De Simone et al. | 568/875 |
| 4,260,829 | 4/1981 | Horner et al. | 502/167 |
| 4,334,983 | 6/1982 | Mentzen | 208/326 |
| 4,383,893 | 5/1983 | Kaibet et al. | 203/41 |

FOREIGN PATENT DOCUMENTS

| | | |
|---|---|---|
| 737621 | 11/1973 | Fed. Rep. of Germany . |
| 0118414 | 3/1975 | Fed. Rep. of Germany . |
| 2839474 | 9/1978 | Fed. Rep. of Germany . |
| 0142539 | 3/1979 | Fed. Rep. of Germany . |
| 0108041 | 7/1982 | Japan . |

Primary Examiner—S. Leon Bashore
Assistant Examiner—V. Manoharan
Attorney, Agent, or Firm—Keil & Weinkauf

[57] ABSTRACT

Distillative separation of liquid mixtures of one or more water-insoluble substances which have boiling points higher than that of water and one or more substances which have boiling points lower than that of water or which form azeotropes having boiling points lower than that of water, wherein the mixture to be distilled is mixed with a quantity of water such that the boiling point of the water under the pressure applied limits the bottom temperature of the mixture of substances to be separated.

2 Claims, 1 Drawing Figure

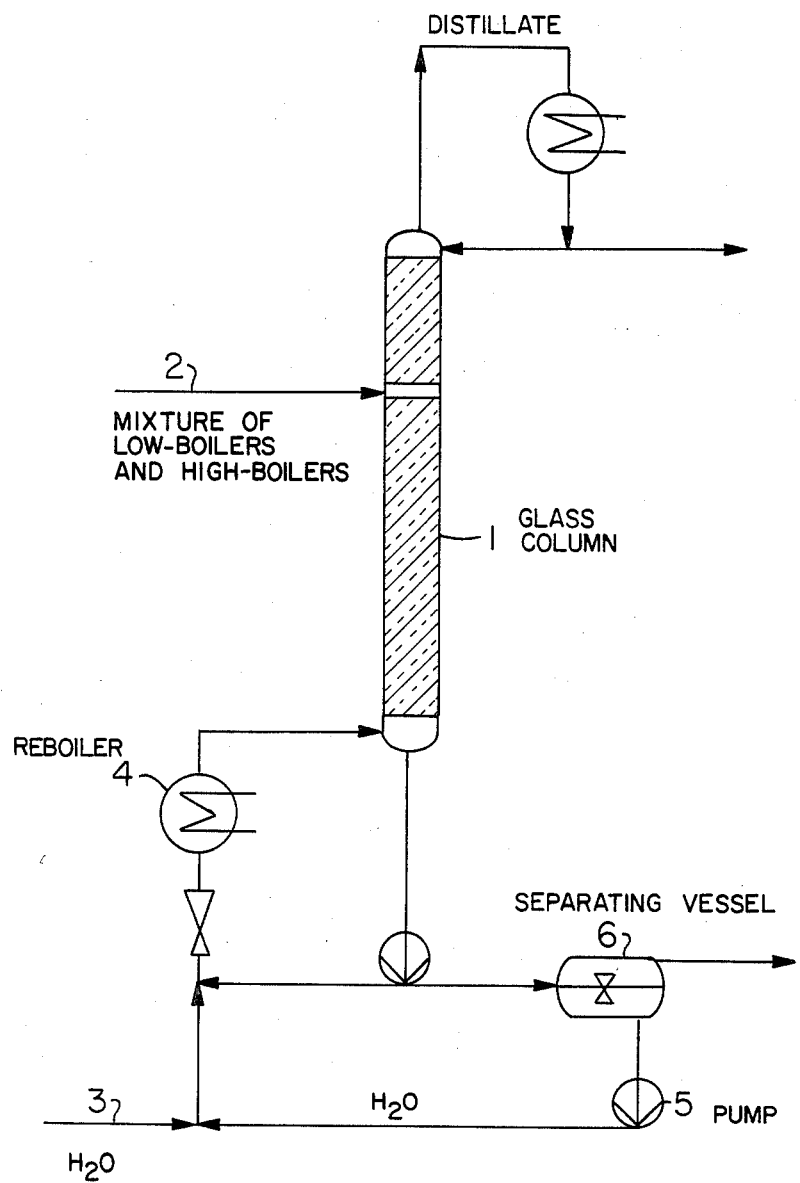

DISTILLATIVE SEPARATION OF LIQUID MIXTURES OF SUBSTANCES

Thermal decomposition of the less volatile substances is a major problem in the distillative separation of mixtures, which is why distillation is preferably used where the more highly volatile (lower-boiling) substance or substances are to be isolated as the useful product.

Although the less volatile (higher-boiling) substance or substances are just as frequently the (or one of the) useful products, in such cases attempts are usually made to distil, for example under reduced pressure, the bottom product remaining after the first distillation, an additional factor being that, even without decomposition having taken place, this bottom product frequently contains by-products, for example from a preceding synthesis, which must be separated off.

There are also cases where the substance or substances of low volatility are very pure, but are very prone to decompose and must, for example, merely be separated from one or more solvents.

In such cases, special distillation apparatus is frequently used, for example thin film evaporators, which are intended to permit gentle separation of the substances. The principle of such apparatus comprises substantially complete gas/liquid mass transfer in an extremely short time, i.e. a combination of large surface area and short residence time.

The disadvantage of such apparatus is its low separation capacity which, from a purely theoretical point of view, cannot exceed the separation capacity of one plate.

Although a column giving appropriate separation can be connected downstream of, or on top of, the thin film evaporator, the problem of having to maintain a particular surface temperature in the evaporator is not solved thereby.

As set out in the claims, we have found that a certain type of frequently occurring mixtures can be separated without problems by fractional distillation, the residue obtained being the useful product.

The mixtures of substances which can be used in the invention are those in which the useful product or products which remain have higher boiling points than that of water (in each case under the same pressure) and are water-miscible or not completely water-miscible, and in which the substance or substances to be distilled off have boiling points lower than that of water.

It is an essential feature of the invention that water is added to such mixtures when carrying out the distillation.

If the original mixture is not completely water-miscible, this is immaterial as long as phase separation occurs during distillation.

It is possible for the water to form an azeotrope with one or all of the substances to be distilled off. In such cases, the corresponding amount of water must be added.

Apart from this particular case, the water is retained within the distillation system, and it is an essential feature of the invention that the water neither distils over by itself nor with the high-boiling substance (in the manner of steam distillation), but refluxes.

The amount of water is also unimportant, just as long as the bottom temperature cannot rise above the boiling point of the water. Theoretically, a few drops are sufficient.

In practice, however, it is desirable that no local overheating can occur, and water should therefore be present almost everywhere in the evaporation vessel. This is best achieved by emulsifying the water with the high-boiling portion of the mixture. In cases where the mixture is initially homogeneous (for example if the low-boiling component is an alcohol or the like), emulsification usually occurs in any case during demixng, at the rate at which material is boiled off. In other cases, adequate distribution can be effected by, for example, stirring.

The invention is of importance in, for example, the isolation of terpenoid scents from solvent-containing mixtures. A number of scents can be produced from citral by, for example, hydrogenation of the double bonds or of the carbonyl group. For example, citronellal can be obtained by hydrogenation of one double bond over a palladium-containing catalyst. Citronellol is obtained from citronellal by hydrogenation of the carbonyl group over a ruthenium-containing catalyst. Hydrogenation of only the carbonyl group gives geraniol from trans-citral and nerol from cis-citral.

In view of the high purity required particularly in the case of scents, it is important to achieve substantially complete conversion to a particular product during synthesis, in order to avoid separation of the starting material from the end product altogether. At the same time, the hydrogenation must of course be very selective, so that the amounts of by-products formed are minimal. In fact, the substances mentioned can be separated from one another only with difficulty, since they have boiling points close together in the region of about 220° C. Other methods, for example extraction processes, have not been proposed.

In order to achieve complete conversion, German Laid-Open Application DOS No. 2,839,474 proposes the presence of a solvent during these hydrogenation reactions, and in particular the addition of a mixture of methanol and, for example, trimethylamine. The amine content of the solvent mixture is from about 10 to 50% by weight, and this amine must of course be removed again completely from the end product. Advantageously, the product is first distilled under atmospheric or slightly reduced pressure to achieve a sufficiently high condensation temperature.

In order to obtain a completely solvent-free useful product, the bottom temperature would have to greatly exceed the maximum permitted bottom temperature, which is from about 90° to 110° C. for citronellal and from about 100° to 130° C. for terpene alcohols, so that decoposition products would be obtained. Formation of such by-products can therefore be avoided only by observing the given upper temperature limits, in which case about 10% of solvent still remains in the particular useful product.

This residual solvent has hitherto been separated off, together with certain lower-boiling by-products, under a pressure of from about 2 to 15 mbar. However, trimethylamine, for example, can no longer be condensed under these conditions, even with brine, but must be removed via the vacuum pump and, for example, washed out of the waste gases or otherwise rendered ineffective. Apart from losses of solvent, other problems connected with temperature control of distillation columns also occur durng continuous operation, and hence it seems desirable to move away from this process.

According to the invention, the products obtained by the hydrogenation of citral can be separated off from methanol and/or trimethylamine, and also any other comparable substances, in a simple manner by addition of water to the distillation, without a relatively high temperature being required.

It is only necessary to ensure adequate emulsification in the bottom of the column. Water has a neutral odor and a sufficiently low boiling point. Since the cost of water is of no significance, it is also of no consequence if it is lost during the purification by distillation. Methanol and trimethylamine can be separated from water without forming an azeotrope.

Since the water is not driven over but only has the effect of controlling the maximum temperature of the mixture, this process is not, as should be emphasized again, a steam distillation. Even if a high-boiling substance should be volatile with steam, the principle can still be applied, since in this case the substance would be condensed in the column section of the unit and driven back.

At first sight, an apparent disadvantage is that water is scarcely miscible with the solvent-free scents. The organic phase in the evaporator contains less than about 0.3% by weight of water, and it could be overheated at the heating surfaces of a normal evaportor and the quality of its smell could thereby be damaged. However, this is avoided if the water content in the evaporator liquid (bottom product) is kept at not less than 10 (for example not more than 40) % by weight and an emulsion, ie. a two-phase intimate mixture, is formed from water and the product mixture so that no zones of low water content can be formed at the heating surfaces. The bottom temperature is thereby restricted to about 100° C.

The emulsification (dispersion) can be effected in a conventional manner by stirrers or, preferably, via an external mixing zone by means of a pump and a nozzle (cf. the FIGURE).

In a particular embodiment, the evaporator is dispensed with entirely and the bottom of the column is charged with heating steam, together with the liquid to be circulated, via a mixing nozzle. The heating steam can also take over the role of drawing the liquid in, if the nozzle is designed as an ejector. The amount of water introduced by condensation of the heating steam must of course be taken into consideration.

The water can be added directly to the bottom of the column. However, it is also possible, in the case of continuous operation, to add the water to the column, for example together with the feed mixture.

The two-phase bottom mixture which is free from methanol and trimethylamine is collected in a separating vessel. The organic phase, which has a constant water content of about 0.3% by weight, is subjected to distillation under reduced pressure, while the aqueous phase is recycled to the solvent distillation. Since only a small amount of water dissolves in the organic phase, only this amount needs replacing during the solvent distillation, unless there is anyway some residual water which has been introduced directly with the heating system.

In order to keep the phase separation vessel small, the water content in the bottom of the column is kept at from about 10 to 40% by weight, in which case a water-in-oil emulsion forms. However, it is also possible substantially to increase the water content and to operate with an oil-in-water emulsion in the evaporator.

EXAMPLE 1

The middle of a 4 m high glass column (1) operated under atmospheric pressure and packed with metal Raschig rings of 8 mm diameter was charged (2) with a mixture of 7.5 kg of citronellal, 5 kg of methanol and 2.5 kg of trimethylamine per hour. At a reflux ratio of 2 and an overhead temperature of 40° C., all of the methanol and trimethylamine were separated off over the top, together with about 0.04 kg/hour of water. 0.2 kg/hour of water were added (3) to the bottom of the column (102° C.). A two-phase bottom liquid containing about 20% by weight of water was thereby formed.

The column was heated via a reboiler (4) with a heating area of 0.4 m$^2$. The forced circulation of the liquid was effected by a centrifugal pump (5) with a circulating capacity of about 1.5 m$^3$/hour.

The bottom product was cooled to about 70° C. and passed to a separating vessel (6). The organic phase was removed and the lower aqueous phase was pumped back into the bottom of the column.

EXAMPLE 2

10 kg/hour of a mixture of 50% of citronellol, 35% of methanol and 15% of trimethylamine were separated continuously under atmospheric pressure in the apparatus described in Example 1. Methanol and trimethylamine containing less than 0.5% of H$_2$O were removed at a reflux ratio of 2 and at an overhead temperature of 45° C.

0.2 kg/hour of water was added to the bottom of the column, the bottom temperature being brought to 95° C.

The two-phase product removed from the bottom was free from amine.

EXAMPLE 3

10 kg/hour of a mixture of 50% of citral, 35% of methanol and 15% of trimethylamine were separated under atmospheric pressure in the apparatus described.

The trimethylamine and methanol and about 0.8% of H$_2$O were removed at a reflux ratio of 0.5 and at an overhead temperature of 40° C.

0.5 l/hour of H$_2$O was metered into the bottom of the column, and the bottom temperature was thus limited to 100° C.

The two-phase bottom product contained only traces of trimethylamine.

We claim:

1. In a process for the separation of methanol and trimethylamine from mixtures containing methanol, trimethylamine and hydrogenation products of citral by distilling off the methanol and the trimethylamine the improvement comprising carrying out the distillation in the presence of water almost completely maintained in the bottoms or refluxed thereto, the concentration of the water being kept between about 10 and 40 weight percent of the distillation bottoms.

2. A process according to claim 1, wherein the water is mechanically dispersed in the bottoms.

* * * * *